US011013701B2

(12) United States Patent
Schiller et al.

(10) Patent No.: US 11,013,701 B2
(45) Date of Patent: May 25, 2021

(54) STABLE FORMULATION FOR PARENTERAL ADMINISTRATION OF TAPENTADOL

(71) Applicant: Gruenenthal GmbH, Aachen (DE)

(72) Inventors: Marc Schiller, Aachen (DE); Carlos van Hemelrijck, Aachen (DE); Stefanie Straub, Bad Vilbel (DE); Eva Wulsten, Willich (DE); Ulrike Bertram, Aachen (DE); Ulrich Reinhold, Aachen (DE)

(73) Assignee: Grünenthal GmbH, Aachen (DE)

( * ) Notice: Subject to any disclaimer, the term of this patent is extended or adjusted under 35 U.S.C. 154(b) by 0 days.

(21) Appl. No.: 15/867,254

(22) Filed: Jan. 10, 2018

(65) Prior Publication Data
US 2018/0125800 A1 May 10, 2018

Related U.S. Application Data

(63) Continuation of application No. 15/078,631, filed on Mar. 23, 2016, now abandoned.

(30) Foreign Application Priority Data

Mar. 27, 2015 (EP) .................................. 15 161 487
May 28, 2015 (EP) .................................. 15 169 730

(51) Int. Cl.
A61K 47/12 (2006.01)
A61K 31/137 (2006.01)
A61K 9/00 (2006.01)
A61K 9/08 (2006.01)
A61P 25/04 (2006.01)

(52) U.S. Cl.
CPC .......... A61K 31/137 (2013.01); A61K 9/0019 (2013.01); A61K 9/08 (2013.01); A61K 47/12 (2013.01); A61P 25/04 (2018.01)

(58) Field of Classification Search
CPC ...... A61K 31/137; A61K 9/08; A61K 9/0019; A61K 47/12; A61P 25/04
See application file for complete search history.

(56) References Cited

U.S. PATENT DOCUMENTS

| 4,775,678 A | 10/1988 | Su et al. |
| 6,183,758 B1 | 2/2001 | Scott |
| 6,248,737 B1 | 6/2001 | Buschmann et al. |
| 6,399,087 B1 | 6/2002 | Zhang et al. |
| 6,638,981 B2 | 10/2003 | Williams et al. |
| 6,992,218 B2 * | 1/2006 | Dietlin .................. A61K 9/0019 564/223 |
| 8,536,130 B2 | 9/2013 | Christoph et al. |
| 9,446,008 B2 | 9/2016 | Reinhold et al. |
| 2003/0191187 A1 | 10/2003 | Lee et al. |
| 2003/0203055 A1 | 10/2003 | Rao et al. |
| 2004/0054012 A1 | 3/2004 | Dietlin et al. |
| 2004/0101263 A1 | 5/2004 | Kundu et al. |
| 2004/0101563 A1 | 5/2004 | Kundu et al. |
| 2004/0180915 A1 | 9/2004 | Gonzales et al. |
| 2005/0058706 A1 | 3/2005 | Bartholomaeus et al. |
| 2005/0070613 A1 | 3/2005 | Dinnequin |
| 2005/0176790 A1 | 8/2005 | Bartholomaus et al. |
| 2005/0186267 A1 | 8/2005 | Thompson et al. |
| 2006/0039864 A1 | 2/2006 | Bartholomaus et al. |
| 2006/0051422 A1 | 3/2006 | Colombo et al. |
| 2006/0111382 A1 | 5/2006 | Shafer et al. |
| 2007/0128412 A1 | 6/2007 | Tso et al. |
| 2007/0213405 A1 | 9/2007 | Fischer et al. |
| 2008/0039405 A1 | 2/2008 | Langley et al. |
| 2008/0075790 A1 | 3/2008 | Kabra et al. |
| 2008/0269326 A1 | 10/2008 | Christoph et al. |
| 2009/0012180 A1 | 1/2009 | Lange et al. |
| 2009/0169631 A1 | 7/2009 | Zamloot et al. |
| 2010/0040559 A1 | 2/2010 | Leiner et al. |

(Continued)

FOREIGN PATENT DOCUMENTS

| AU | 2005259478 B2 | 7/2010 |
| CA | 2 572 352 A1 | 1/2006 |

(Continued)

OTHER PUBLICATIONS

Imperfect Gases' at www4.ncsu.edu/~franzen/public_html/CH433/lecture/Imperfect_Gases_Detail.pdf (initially retrieved from the interne Dec. 13, 2016 (Year: 2016).*
O'Lenick et al, "Comparatively Speaking: Newtonian vs. Non-newtonian Liquids", (https://www.cosmeticsandtoiletries.com/formulating/function/viscositymod/3762622.html) Oct. 13, 2008.
Alfonso, G.R., "Remington Farmacia," p. 2,415 (1998) and translation thereof.
American Academy of Pediatrics (Feb. 2, 1997). "Inactive Ingredients in Pharmaceutical Products: Update (Subject Review)." Pediatrics, 99: 268-278.
Bibliographic data for Japanese Patent Application No. 2010-520907 A.
Bibliographic data information for PCT International Publication No. WO 2010/096045 A1.

(Continued)

Primary Examiner — Dennis Heyer
(74) Attorney, Agent, or Firm — Norris McLaughlin, P.A.

(57) ABSTRACT

The invention relates to an aqueous pharmaceutical composition for parenteral administration comprising Tapentadol or a physiologically acceptable salt thereof, wherein the concentration of Tapentadol is within the range of from 0.10 to 8.00 mg/mL, based on the weight of Tapentadol free base and based on the total volume of the composition; and wherein the pH value of the composition is buffered and within the range of from 4.0 to 6.0. The invention also relates to a container comprising the pharmaceutical composition and a process for the preparation thereof. The invention also relates to a kit comprising the contained according to the invention in a packaging. The pharmaceutical composition according to the invention is particularly useful for treating pain, especially acute pain, preferably in pediatric patients.

22 Claims, No Drawings

(56) References Cited

U.S. PATENT DOCUMENTS

| | | | |
|---|---|---|---|
| 2010/0227921 A1 | 9/2010 | Franklin et al. | |
| 2010/0272815 A1 | 10/2010 | Khunt et al. | |
| 2010/0311842 A1 | 12/2010 | Christoph et al. | |
| 2011/0098284 A1 | 4/2011 | Babul | |
| 2011/0190267 A1 | 8/2011 | Franklin et al. | |
| 2012/0201891 A1 | 8/2012 | Cottrell et al. | |
| 2012/0225951 A1* | 9/2012 | Christoph | A61K 9/0019 514/654 |
| 2012/0270848 A1 | 10/2012 | Mannion et al. | |
| 2013/0022670 A1* | 1/2013 | Reinhold | A61K 9/0095 424/451 |
| 2013/0237608 A1 | 9/2013 | Bartholomaeus et al. | |
| 2013/0273152 A1 | 10/2013 | Draget et al. | |
| 2016/0106688 A1 | 4/2016 | Christoph et al. | |
| 2018/0125800 A1 | 5/2018 | Schiller et al. | |
| 2018/0221308 A1 | 8/2018 | Bartholomaeus et al. | |
| 2019/0290603 A1 | 9/2019 | Lange et al. | |

FOREIGN PATENT DOCUMENTS

| | | |
|---|---|---|
| CA | 2 572 532 A1 | 1/2006 |
| CA | 2 725 635 A1 | 1/2006 |
| CA | 2 439 269 C | 11/2011 |
| CN | 101495447 A | 7/2009 |
| CN | 102711726 A | 10/2012 |
| CN | 103501775 A | 1/2014 |
| CN | 103735500 A | 4/2014 |
| EA | 201300988 A1 | 6/2014 |
| EP | 0 147 222 A2 | 7/1985 |
| EP | 0 147 223 A2 | 7/1985 |
| EP | 391369 B1 | 10/1990 |
| EP | 0 693 475 A1 | 1/1996 |
| EP | 1 612 203 B1 | 8/2007 |
| EP | 2 117 525 A1 | 11/2009 |
| JP | S 60-156602 A | 8/1985 |
| JP | 2002-316926 A | 10/2002 |
| JP | 2004-516265 A | 6/2004 |
| JP | 2004-527491 A | 9/2004 |
| JP | 2006-512344 A | 4/2006 |
| JP | 2008-266168 A | 11/2008 |
| JP | 2008-539269 A | 11/2008 |
| JP | 2010-520907 A | 6/2010 |
| JP | 2010-536712 A | 12/2010 |
| JP | 2011-506342 A | 3/2011 |
| JP | 2013-527152 A | 6/2013 |
| MX | PA03007712 A | 3/2004 |
| RU | 2 309 942 C2 | 11/2007 |
| WO | WO 01/22998 A1 | 4/2001 |
| WO | WO 01/93830 A1 | 12/2001 |
| WO | WO 02/067651 A2 | 9/2002 |
| WO | WO 02/067916 A2 | 9/2002 |
| WO | WO 02/072080 A2 | 9/2002 |
| WO | WO 03/035053 A1 | 3/2003 |
| WO | WO 03/041687 A2 | 5/2003 |
| WO | WO 2004/062689 A1 | 7/2004 |
| WO | WO 2006/002886 A1 | 1/2006 |
| WO | WO 2006/116626 A2 | 11/2006 |
| WO | WO 2007/128412 A1 | 11/2007 |
| WO | WO 2007/128413 A1 | 11/2007 |
| WO | WO 2008/012283 A1 | 1/2008 |
| WO | WO 2008/110323 A1 | 9/2008 |
| WO | 2008/128740 A1 | 10/2008 |
| WO | WO 2008/135601 A2 | 11/2008 |
| WO | WO 2009/067703 A2 | 5/2009 |
| WO | WO 2009/092601 A1 | 7/2009 |
| WO | WO 2009/124586 A1 | 10/2009 |
| WO | WO 2010/089767 A1 | 8/2010 |
| WO | WO 2010/096045 A1 | 8/2010 |
| WO | WO 2010/122442 A1 | 10/2010 |
| WO | WO 2011/016487 A1 | 2/2011 |
| WO | WO 2011/071400 A1 | 6/2011 |
| WO | WO 2011/128630 A2 | 10/2011 |
| WO | WO 2012/119727 A1 | 9/2012 |
| WO | WO 2012/119728 A1 | 9/2012 |
| WO | WO 2012/119729 A1 | 9/2012 |
| WO | WO 2013/144814 A1 | 10/2013 |
| WO | WO 2014/005546 A1 | 1/2014 |
| WO | WO 2014/191710 A1 | 12/2014 |
| WO | WO 2015/113200 A1 | 8/2015 |
| WO | WO 2016/156147 A1 | 10/2016 |

OTHER PUBLICATIONS

Bibliographic data information for PCT international Publication No. WO 2011/128630 A2.
Bibliographic information for Japanese Patent Application No. 2004-527491 A.
Christoph, T., et al., "Tapentadol, but Not Morphine, Selectively Inhibits Disease-Related Thermal Hyperalgesia in a Mouse Model of Diabetic Neuropathic Pain", Neuroscience Letters, 470, 2010, Elsevier Ireland Ltd., pp. 91-94 (Four (4) pages).
Ecuadorian Patent Document No. SP-06-7097, dated Dec. 19, 2006 (related to European Patent No. 1 612 203 B1).
Ecuadorian Patent Document No. SP-06-7117, dated Dec. 26, 2006 (related to U.S. Patent Application Publication No. US 2006/0039864 A1).
Ecuadorian Patent Document No. SP-08-8793, dated Oct. 6, 2008 (related to PCT International Publication No. WO 2007/128413 A1).
Ecuadorian Patent Document No. SP-08-8873, dated Nov. 11, 2008 (related to PCT International Publication No. WO 2007/128412 A1).
English translation of Japanese Patent Application No. 2002-316926 A.
English translation of Japanese Patent Application No. 2008-266168 A.
European Pharmacopoeia 7.0, "5.1.3 Efficacy of Antimicrobial Preservation"; 2011; pp. 505-506.
Extended Search Report dated Mar. 23, 2017, and issued in connection with European Patent Application No. 16190255.6.
Fude, Cui; "Pharmacy", People's Medical Publishing House, 2004, p. 59.
Kumar, R, et al., Development and Characterization of Novel Trans Buccoadhesive Bilayer Tablets of Tapentadol Hydrochloride, Asian Journal of Research in Pharmaceutical Science, vol. 3, Issue, 2 (2013)—Abstract.
"Remington Essentials of Pharmaceutics" (Felton, L.A., ed.) Pharmaceutical Press (2013).
Schroeder, W., et al., "Differential Contribution of Opioid and Noradrenergic Mechanisms of Tapentadol in Rat Models of Nociceptive and Neuropathic Pain", European Journal of Pain, 14, 2010, European Federation of International Association for the Study of Pain Chapters, Published by Elsevier Ltd., pp. 814-821 (Eight (8) pages).
Tamanai-Shacoori et al.(2007) "The Antibacterial Activity of Tramadol Against Bacteria Associated with Infectious Complications After Local or Regional Anesthesia." Anesth. Analg. 105: 524-27.
Tzschentke, T., et al., "(−)-(1R, 2R)-3-(3-Dimethylamino-1-ethyl-2-methyl-propyl)-phenol Hydrochloride (Tapentadol NCl): a Novel μ-Opioid Receptor Agonist/Norepinephrine Reuptake Inhibitor with Broad-Spectrum Analgesic Properties", The Journal of Pharmacology and Experimental Therapeutics, 2007, vol. 323, No. 1, pp. 265-276 (Twelve (12) pages).
U.S. Appl. No. 13/410,768, filed Mar. 2, 2012.
U.S. Appl. No. 13/410,837, filed Mar. 2, 2012.
U.S. Appl. No. 13/410,945, filed Mar. 2, 2012.
U.S. Appl. No. 15/867,330, filed Jan. 10, 2018.
U.S. Appl. No. 14/981,223, filed Dec. 28, 2015.
U.S. Appl. No. 15/093,522, filed Apr. 7, 2016.
U.S. Appl. No. 15/232,841, filed Aug. 10, 2016.
U.S. Appl. No. 15/712,812, filed Sep. 22, 2017.
U.S. Appl. No. 15/867,254, filed Jan. 10, 2018.
U.S. Appl. No. 16/662,392, filed Oct. 24, 2019.
U.S. Appl. No. 16/818,275, filed Mar. 13, 2020.
Yu et al. "Newly Edited Manual of Medicines for External Use"; Shandong Science and Technology Press, 1996, p. 54.

(56) References Cited

OTHER PUBLICATIONS

Zhang, Q., 2005, pp. 92-117 with partial English Translation (Twenty-eight (28) pages).
European Search Report dated Sep. 27, 2011 for EP 11003601.
European Search Report dated Jan. 16, 2018 for EP 1719271.
European Search Opinion dated Jan. 16, 2018 for EP 1719271.
European Search Report dated Nov. 25, 2019 for EP 19187973.
European Search Opinion dated Nov. 25, 2019 for EP 19187973.
International Search report dated Jan. 6, 2012 for PCT/EP2012/000905.
International Search report dated Jan. 6, 2012 for PCT/EP2012/000904.
International Preliminary Report on Patentability dated Sep. 10, 2013 for PCT/EP2012/000904.
European Search Reported dated Sep. 27, 2011 for EP 11003602.
European Search Reported dated Feb. 17, 2016 for EP 1520814.
European Search Opinion dated Feb. 17, 2016 for EP 1520814.
International Search Report dated Sep. 10, 2013 for PCT/EP2012/000905.
International Preliminary Report on Patentability dated Sep. 10, 2013 for PCT/EP2012/000905.
European Search Report issued in counterpart European Application No. 15169730.7 dated Aug. 11, 2015 (six pages).
Tzschentke et al., "Tapentadol Hydrochloride Analgesic Mu-Opioid Receptor Agonist Noradrenaline Reuptake Inhibitor" Dec. 2006, pp. 1053-1061, vol. 31, No. 12, Drugs of the Future, XP-002660111.
Imperfect Gases at http://www4.ncsu.edu/-franzen/public_html/CH433/lecture/Imperfect_Gases_Detail.pdf (retrieved from the internet on Dec. 13, 2016).
de Villiers, M. "Antimicrobial Preservatives" in Thompson, J.E., et al. "A Practical Guide to Contemporary Pharmacy Practice," 3rd ed., pt. 4, ch. 16, pp. 203-215 (2009).
Preservation Efficacy Test Certificate of Analysis for sodium benzoate 1.5 mg/ml (2020).
Submission dated Jul. 15, 2019, in connection with European Patent Application No. 17 189 271.4.
Preservation Efficacy Test Certificate of Analysis for benzoic acid 2 mg/ml (2020).
Opposition papers dated Jan. 28, 2021, in connection with European Patent No. 3287123 B1.
Buelbring, E., et al. "Biological Comparison of Local Anaestetics," J. Pharmacol. Exp. Ther. 85:78-41 (1945).
Extended European Search Report for App. No. EP 11003601.9-2112, dated Oct. 12, 2011.
Ho et al., "In Vitro Effects Preservatives in Nasal Sprays on Human Nasal Epithelial Cells", American Journal of Rhinology, 2008, vol. 22, No. 2, pp. 125-129.
Hong et al., "Allergy to Ophthalmic Preservatives", Current Opinion in Allergy and Clinical Immunology, 2009, vol. 9, pp. 447-453.
Lippincott et al. (Fluids & Electrolytes—An Incredibly Easy Pocket Guide, (2006), Lippincott, Williams, and Wilkins, Ambler PA, pp. 179-181).
Liu, "Pharmacology and clinical application of analgesic tapentadol with a dual mode of action," Pain Clin J., 2008, pp. 293-298, vol. 4, No. 4.
Mehta et al. (Mar. 20210) "# 228 Tapentadol." Retrieved on Oct. 16, 2014. Retrieved from the Internet <URL: http://www.eperc.mcw.edu/EPERC/FastFactsIndex/ff_228.htm>.
Oishi, "Effects of Propyl Paraben on the Male Reproductive System", Food and Chemical Toxicology, 2002, vol. 40, No. 12, pp. 1807-1813.
Ramanath Royal, B., "Pharmaceutical Aspects of Tapentadol," Int. J. Pharm. Bioscience 3:79-84 (2012).
Soni et al., "Safety Assessment of Esters of p-hydroxybenzoic Acid (parabens)", Food and Chemical Toxicology, 2005, vol. 43, No. 7, pp. 985-1015.
Soni et al., "Safety Assessment of Propyl Paraben: a Review of the Published Literature", Food and Chemical Toxicology, 2001, vol. 39, No. 6, pp. 513-532.
U.S. Appl. No. 16/545,567, filed Aug. 20, 2019.

* cited by examiner

STABLE FORMULATION FOR PARENTERAL ADMINISTRATION OF TAPENTADOL

This application is a continuation of U.S. application Ser. No. 15/078,631, filed Mar. 23, 2016, which claims priority from European Application No. 15 169 730.7, filed May 28, 2015 and European Application No. 15 161 487.2, filed Mar. 27, 2015, the entire disclosures of which are herein expressly incorporated by reference.

The invention relates to an aqueous pharmaceutical composition for parenteral administration comprising Tapentadol or a physiologically acceptable salt thereof, wherein the concentration of Tapentadol is within the range of from 0.10 to 8.00 mg/mL, based on the weight of Tapentadol free base and based on the total volume of the composition; and wherein the pH value of the composition is buffered and within the range of from 4.0 to 6.0. The invention also relates to a container comprising the pharmaceutical composition and a process for the preparation thereof. The invention also relates to a kit comprising the contained according to the invention in a packaging. The pharmaceutical composition according to the invention is particularly useful for treating pain, especially acute pain, preferably in pediatric patients.

Various formulations for parenteral administration are known from the prior art.

WO 01/22998 discloses a therapeutic calcitriol solution which is suitable for packaging into pharmaceutical vials without producing discoloration of the antioxidant component of the solution.

WO 01/93830 relates to a method for obtaining aqueous formulations with easily oxidizable active principles, notably phenols, stable over prolonged period, which consists of subjecting them to extreme deoxygenation by bubbling with an inert gas and/or placing under vacuum, protecting them against possible resorption of oxygen by keeping them under an inert gas atmosphere by filling, under inert gas, into bottles previously cleared of air by insufflation with inert gas, then subjecting them, whilst stoppering, to low pressure as obtained in the bottle, of 65,000 Pa maximum, and thus obtaining aqueous solutions having a residual oxygen concentration in the solution below 2 ppm, and preferably of the order of 1 ppm and even 0.5 ppm.

WO 02/072080 relates to parenterally administrable, especially infusible, aqueous paracetamol solutions which are stable in storage and free of particles and discoloration. Said solutions contain a mixture of: a) between 1 and 17 grams of paracetamol per liter, and b) between 0.01 and 0.17 grams of at least one physiologically compatible antioxidant per liter, selected from the group comprising ascorbic acid, N-acetyl-L-cysteine and stabilizer compounds containing SH groups which are different from N-acetyl-L-cysteine. The aqueous solution is free of organic solvents and has a pH value of between 5.5 and 6.5 and an oxygen content of less than 0.5 milligrams per liter.

WO 03/041687 a method for producing stabilized antioxidant-free solutions based on phenolic substances which consists in: deoxygenation of the solutions with an inert gas, and in deoxygenation of gas holdups of the vessels, of the manufacturing pipes and inerting of ampoules and flasks containing the solute with a dense inert rare gas such as argon, at low temperature and with pH adjusted above 3.0 and below 5.0 to obtain stable solutions of phenolic substances containing not more than 0.02 ppm of oxygen in the solution, which is filtered by double sterilizing filtration.

WO 2004/062689 discloses stabilized aqueous compositions of tissue factor pathway inhibitor (TFPI) or TFPI variants that comprise a solubilizing agent, an antioxidant, and a buffer. The combination of a solubilizing agent and an antioxidant can lead to a significant improvement in the storage life of TFPI or TFPI variant compositions. The solubilizing agent and antioxidant substantially counteract the effects of TFPI or TFPI variant degradation through aggregation and oxidation.

WO 2008/135601 relates to a liquid formulation, stable to oxidation, based on a phenolic active principle susceptible to oxidation such as paracetamol in an aqueous solvent and to a method for preparing such formulation. The formulation and the method are characterized in that the active principle is admixed in the aqueous solvent having a temperature between 60° C. and 105° C., a pH between 5.0 and 6.0 and an oxygen concentration below 0.0002%.

WO 2009/124586 concerns a stable aqueous pharmaceutical composition comprising 5-[(2RS)-2-cyclopropyl-7,8-dimethoxy-2H-1-benzopyran-5-ylmethyl]-pyrimidine-2,4-diamine in form of the water soluble methanesulfonic acid salt, a physiological sodium chloride solution, ethanol and Povidone 12 PF, the liquid having a pH of over and above 4.8, but not higher than 5.2, and wherein the oxygen amount is controlled to be 0.8 ppm or less; which can be sterilized by filtration and/or by heated treatment, stored for longer time periods and which can be used for bolus injection or diluted for i.v. infusion.

WO 2011/071400 relates to stable liquid formulations of paracetamol for pharmaceutical use and to a method of preparation of stable paracetamol solutions.

WO 2013/144814 discloses a stable ready-to-use pharmaceutical composition comprising pemetrexed or pharmaceutically acceptable salts thereof, wherein the composition is free from antioxidants, amino acids and chelating agents. Also provided is a process for preparing a stable ready-to-use pharmaceutical composition comprising the steps: i) purging inert gas into a parenterally acceptable aqueous solvent until the dissolved oxygen content of the solvent comes to less than 7 mg/L, preferably less than 3 mg/L; ii) adding pemetrexed disodium under stirring; iii) adjusting the pH of the resulting solution to between 4 to 9; iv) optionally adding additional aqueous solvent; wherein the composition is purged with inert gas throughout the entire process.

Pharmaceutical dosage forms of Tapentadol are also known from the prior art, e.g., WO 02/67651, WO 03/035053, WO 2006/002886, WO 2007/128412, WO 2007/128413, WO 2008/110323, WO 2009/067703, WO 2009/092601, US 2010/272815, and T. M. Tzschentke et al., Drugs of the future, 31(12), 2006, 1053-1061.

WO 2012/119727 relates to an aqueous pharmaceutical composition containing tapentadol or a physiologically acceptable salt thereof and being adapted for oral administration. The composition has excellent storage stability without relying on the presence of high amounts of preservatives.

WO 2012/119728 discloses parenteral formulations for the administration of Tapentadol. The concentration of Tapentadol in these formulations is preferably below 100 mg/mL. The concentration of Tapentadol in the exemplified formulations according to WO 2012/119728 is 15 mg/mL and 20 mg/mL, respectively. According to WO 2012/119728 Tapentadol exhibits antimicrobial properties. These antimicrobial properties are more pronounced at higher pH values. In consequence, preservatives may be omitted or their content in the formulations may at least be decreased. The complete absence of preservatives is preferred when the content of Tapentadol is sufficiently high so that due to its preserving property the desired shelf life or in use stability can be achieved by the presence of Tapentadol itself. For that purpose, the concentration of Tapentadol is preferably at least 10 mg/mL, based on the total volume of the composition.

It has been found, however, that in diluted solutions the dissolved Tapentadol tends to decomposition having a negative impact on storage stability of parenteral formulations at such low concentrations of Tapentadol.

It is an object of the invention to provide parenteral formulations of Tapentadol that have advantages compared to the parenteral formulations of Tapentadol of the prior art. The parenteral formulations should contain Tapentadol or physiologically acceptable salts thereof at comparatively low concentrations but at the same time should have a good storage stability and shelf life.

This object has been achieved by the subject-matter of the patent claims.

It has been surprisingly found that in diluted solutions at pH values in the range of 6 to 7.5 the otherwise chemically very stable pharmacologically active ingredient Tapentadol is subject to inacceptable chemical degradation. The inventors have unexpectedly found that chemical stability can be substantially improved by lowering the pH value and by increasing the buffer capacity in order to provide an adjusted and robustly maintained pH value. While conventional diluted solutions of Tapentadol are instable and show a successive increase of the pH value after autoclaving and long-term storage, the pH value of the composition according to the invention remains substantially unchanged.

Therefore, it has been surprisingly found that at comparative low concentrations of Tapentadol below 8.0 mg/mL, especially below 5.0 mg/mL, particularly at concentrations of about 1.0 mg/mL, lowering the pH value of the pharmaceutical composition for parenteral administration has a stabilizing effect so that decomposition (degradation) of Tapentadol can be significantly reduced or even suppressed, also under stress conditions after repeated autoclaving. Thus, it appears that under certain conditions antimicrobial effect of Tapentadol on the one hand (cf. WO 2012/119728) and chemical stability of Tapentadol on the other hand are both function of the pH value but in opposite directions.

Further, it has been surprisingly found that even at pH values of the composition within the range of from 4.0 to 6.0 and even at such comparative low concentrations of Tapentadol, stable pharmaceutical compositions for parenteral administration can be provided that need neither a preservative nor an antioxidant and are nevertheless storage stable for a long period of time. This is particularly surprising, as the antimicrobial effect of Tapentadol itself is a function of its concentration and of the pH value such that the antimicrobial effect of Tapentadol should principally decrease when its concentration and the pH value are comparatively low.

Still further, it has been surprisingly found that the composition remains chemically stable under the harsh conditions of autoclaving, e.g. for at least 20 min at 2 bar and 121° C. Thus, the storage stability of the composition according to the invention does not need to rely on the antimicrobial effect of Tapentadol alone. Autoclaving achieves sufficient storage stability against antimicrobial decontamination without the need for preservatives.

Furthermore, it has been surprisingly found that Tapentadol may be sufficiently stabilized against chemical decomposition by degassing and providing the composition under an inert gas atmosphere, respectively, e.g. by means of degassing with nitrogen purge. The use of antioxidants can thus be avoided.

A first aspect of the invention relates to a stable aqueous pharmaceutical composition for parenteral administration comprising Tapentadol or a physiologically acceptable salt thereof, wherein the concentration of Tapentadol is within the range of from 0.10 to 8.00 mg/mL, preferably within the range of from 0.10 to 5.00 mg/mL, more preferably within the range of from 0.50 to 1.50 mg/mL, based on the weight of Tapentadol free base and based on the total volume of the composition; wherein the pH value of the composition is buffered, preferably by a citrate buffer, and wherein the pH value is within the range of from 4.0 to 6.0, preferably within the range of from 4.5 to 5.5, in particular before and after autoclaving. Thus, preferably the composition according to the invention has undergone autoclaving, preferably at least for at least 20 minutes at least at 2 bar and at least at 121° C., and the pH value before autoclaving as well as the pH value after autoclaving is independently within the range of from 4.0 to 6.0, preferably within the range of from 4.5 to 5.5.

The term "pharmaceutical composition" includes any pharmaceutical preparation or formulation that is customized for being administered to a human being or animal Preferably, the composition is an aqueous solution.

Unless expressly stated otherwise, all percentages are weight percent, relative to the total weight of the pharmaceutical composition according to the invention.

Unless expressly stated otherwise, all values in mL refer to the total volume of the pharmaceutical composition according to the invention.

Unless expressly stated otherwise, parameters and conditions (such as temperature, pressure, relative humidity, volume, weight, concentration, pH value, titration acidity, buffer capacity, osmolarity, content of molecular oxygen, storage stability, color, and the like) are determined and measured in accordance with the requirements and recommendations as set forth in the European Pharmacopoeia (Ph. Eur.). Unless expressly stated otherwise, all references to Ph. Eur. refer to the version that is officially valid in March 2015. General conditions are typically ambient conditions.

For the purpose of the specification, the term "Tapentadol" includes the free base ((1R,2R)-3-(3-dimethylamino-1-ethyl-2-methyl-propyl)-phenol) as well as any physiologically acceptable salt thereof, particularly the hydrochloride ((1R,2R)-3-(3-dimethylamino-1-ethyl-2-methyl-propyl)-phenol hydrochloride).

Thus, unless expressly stated otherwise, the term "Tapentadol" does not only refer to the free base but also to any physiologically acceptable salt. Further, unless expressly stated otherwise, all amounts, contents and concentrations are equivalents related to Tapentadol free base.

Preferably, Tapentadol is present in the composition according to the invention as Tapentadol hydrochloride. In a preferred embodiment, Tapentadol is present as solubilized Tapentadol hydrochloride salt form A. Form A of Tapentadol hydrochloride is known from the prior art. In this regard, it can be referred to e.g. US 2007/0213405. Preferably, form A is characterized by showing at least one or more X-ray lines (2-theta values) in a powder diffraction pattern when measured using Cu Kα radiation selected from the list comprising 15.1±0.2, 16.0±0.2, 18.9±0.2, 20.4±0.2, 22.5±0.2, 27.3±0.2, 29.3±0.2 and 30.4±0.2

The concentration of Tapentadol is within the range of from 0.10 to 8.00 mg/mL, preferably within the range of from 0.10 to 5.00 mg/mL, more preferably within the range of from 0.50 to 1.50 mg/mL, based on the weight of Tapentadol free base and based on the total volume of the composition. In preferred embodiments, said concentration is within the range of 1.0±0.8 mg/mL, or 1.0±0.7 mg/mL, or 1.0±0.6 mg/mL, or 1.0±0.5 mg/mL, or 1.0±0.4 mg/mL, or 1.0±0.3 mg/mL, or 1.0±0.2 mg/mL, or 1.0±0.1 mg/mL.

The composition according to the invention is aqueous, i.e. the composition comprises water which is typically water for injection purposes, i.e. highly pure and sterile water.

Preferably, the water content is at least 50 wt.-%, more preferably at least 60 wt.-%, still more preferably at least 70 wt.-%, yet more preferably at least 80 wt.-%, most preferably at least 85 wt.-% and in particular at least 90 wt.-%, based on the total weight of the composition.

Preferably, the water content is at least 95 wt.-%, more preferably at least 96 wt.-%, still more preferably at least 97 wt.-%, yet more preferably at least 98 wt.-%, most preferably at least 99 wt.-% and in particular at least 99.5 wt.-%, based on the total weight of the composition.

In preferred embodiments, the water content is within the range of from 99.020±0.970 wt.-%, or 99.020±0.900 wt.-%, or 99.020±0.800 wt.-%, or 99.020±0.700 wt.-%, or 99.020±0.600 wt.-%, or 99.020±0.500 wt.-%, or 99.020±0.400 wt.-%, or 99.020±0.300 wt.-%, based on the total weight of the composition.

Besides water, the composition according to the invention may contain further solvents.

Further suitable solvents include all types of physiologically acceptable hydrophilic solvents, preferably selected from the group consisting of ethanol, glycerol, propylene glycol, 1,3-butanediol and macrogol 300.

Preferably, however, the composition according to the invention does not contain further solvents besides water.

The pH value of the composition according to the invention is buffered, i.e. the composition comprises a buffer (i.e. a pair of conjugate acid and conjugate base).

Preferred buffers are derived from the following acids: organic acids such as acetic acid, propionic acid, maleic acid, fumaric acid, lactic acid, malonic acid, malic acid, mandelic acid, citric acid, tartaric acid, succinic acid; or inorganic acids such as phosphoric acid. When the buffer is derived from any of the above acids, the buffer constitutes of said acid and its conjugate base(s). Buffers derived from acetic acid, citric acid, lactic acid, succinic acid or phosphoric acid are particularly preferred.

A skilled person is fully aware that multiprotonic acids can form more than a single pair of a conjugate acid and a conjugate base. For example, citric acid is a triprotonic acid so that it forms the following pairs of conjugate acid and conjugate base: (i) citric acid—dihydrogencitrate, (ii) dihydrogencitrate—hydrogencitrate, (iii) and hydrogencitrate—citrate. In other words, any of citric acid, dihydrogencitrate and hydrogencitrate can be the acid of a buffer with the conjugate base. A skilled person is also fully aware that the conjugate acids and conjugate bases are in equilibrium with one another and that the predominant species that are present in a mixture of citrate, hydrogencitrate, dihydrogencitrate and citric acid can be determined on the basis of the pKA values and the pH value of the composition.

For the purpose of the specification, the expression "buffer" refers to the total quantity of conjugate acids and conjugate bases. For example, when the buffer is derived from citric acid, i.e. is a citrate buffer, the expression "buffer" refers to the total quantity of citrate, hydrogencitrate, dihydrogencitrate and citric acid. Further, a skilled person is fully aware that a buffer, e.g. citric acid as conjugate acid and sodium dihydrogencitrate as conjugate base, can be established either by adding citric acid and an appropriate amount of sodium hydroxide, or sodium citrate and an appropriate amount of hydrochloric acid, or citric acid and sodium dihydrogencitrate as such. Unless expressly stated otherwise, "sodium citrate" is synonymous to "trisodium citrate". Sodium citrate dihydrate (=trisodium citrate dihydrate) thus has the linear formula $HOC(COONa)(CH_2COONa)_2 \cdot 2H_2O$ and a relative molecular weight of 294.10 g/mol.

Accordingly, in case that the composition contains an appropriate amount of Tapentadol in form of its hydrochloride, a buffer can be established by adding sodium citrate, e.g. in form of sodium citrate dihydrate. Nevertheless, Tapentadol and its physiologically acceptable salts are not to be considered as conjugate acid or conjugate base of the buffer.

Preferably, the concentration of the buffer, preferably sodium citrate or its dihydrate, is adjusted to provide a sufficient buffer capacity.

It has been surprisingly found that by adjusting the content of buffer in the pharmaceutical composition, the shelf life can be substantially improved, particularly the chemical stability of Tapentadol in the composition at its comparatively low concentrations, particularly also under conditions of autoclaving. It has been found that an optimal buffer concentration can be found that on the one hand provides sufficient stability of the composition, but that on the other had does not entrain significant amounts of material into the organism to be treated and does not significantly change the pH value of the body fluids of the organism to be treated.

Preferably, the composition according to the invention comprises a buffer comprising one or more conjugate bases and one or more conjugate acids selected from the group consisting of citrate, hydrogencitrate, dihydrogencitrate and citric acid.

In preferred embodiments, the composition according to the invention comprises a buffer comprising one or more conjugate bases and one or more conjugate acids and having a concentration of at least 0.015 wt.-%, more preferably at least 0.020 wt.-%, still more preferably at least 0.025 wt.-%, and most preferably at least 0.030 wt.-%, based on the total weight of the one or more conjugate bases and the one or more conjugate acids and based on the total weight of the composition.

In preferred embodiments, the composition according to the invention comprises a buffer comprising one or more conjugate bases and one or more conjugate acids and having a concentration of not more than 0.055 wt.-%, more preferably not more than 0.050 wt.-%, still more preferably not more than 0.045 wt.-%, yet more preferably not more than 0.040 wt.-%, and most preferably not more than 0.035 wt.-%, based on the total weight of the one or more conjugate bases and the one or more conjugate acids and based on the total weight of the composition.

In preferred embodiments, the composition according to the invention comprises a buffer comprising one or more conjugate bases and one or more conjugate acids and having a concentration within the range of from 0.015 to 0.055 wt.-%, more preferably within the range of from 0.020 to 0.050 wt.-%, still more preferably within the range of from 0.025 to 0.045 wt.-%, most preferably within the range of from 0.030 to 0.045 wt.-%, based on the total weight of the one or more conjugate bases and the one or more conjugate acids and based on the total weight of the composition.

In a preferred embodiment, the content of the buffer, preferably sodium citrate or its dihydrate, is within the range of from 0.020±0.018 wt.-%, or 0.020±0.016 wt.-%, or 0.020±0.014 wt.-%, or 0.020±0.012 wt.-%, or 0.020±0.010 wt.-%, or 0.020±0.008 wt.-%, or 0.020±0.006 wt.-%, or 0.020±0.004 wt.-%, based on the total weight of the one or more conjugate bases and the one or more conjugate acids and based on the total weight of the composition.

In another preferred embodiment, the content of the buffer, preferably sodium citrate or its dihydrate, is within the range of from 0.030±0.018 wt.-%, or 0.030±0.016 wt.-%, or 0.030±0.014 wt.-%, or 0.030±0.012 wt.-%, or 0.030±0.010 wt.-%, or 0.030±0.008 wt.-%, or 0.030±0.006 wt.-%, or 0.030±0.004 wt.-%, based on the total weight of the one or more conjugate bases and the one or more conjugate acids and based on the total weight of the composition.

In still another preferred embodiment, the content of the buffer, preferably sodium citrate or its dihydrate, is within the range of from 0.040±0.035 wt.-%, or 0.040±0.030 wt.-%, or 0.040±0.025 wt.-%, or 0.040±0.020 wt.-%, or 0.040±0.015 wt.-%, or 0.040±0.010 wt.-%, or 0.040±0.005 wt.-%, based on the total weight of the one or more conjugate bases and the one or more conjugate acids and based on the total weight of the composition.

In yet another preferred embodiment, the content of the buffer, preferably sodium citrate or its dihydrate, is within the range of from 0.060±0.035 wt.-%, or 0.060±0.030 wt.-%, or 0.060±0.025 wt.-%, or 0.060±0.020 wt.-%, or 0.060±0.015 wt.-%, or 0.060±0.010 wt.-%, or 0.060±0.005 wt.-%, based on the total weight of the one or more conjugate bases and the one or more conjugate acids and based on the total weight of the composition.

In still another preferred embodiment, the content of the buffer, preferably sodium citrate or its dihydrate, is within the range of from 0.080±0.035 wt.-%, or 0.080±0.030 wt.-%, or 0.080±0.025 wt.-%, or 0.080±0.020 wt.-%, or 0.080±0.015 wt.-%, or 0.080±0.010 wt.-%, or 0.080±0.005 wt.-%, based on the total weight of the one or more conjugate bases and the one or more conjugate acids and based on the total weight of the composition.

In a particularly preferred embodiment, the content of the buffer, preferably sodium citrate or its dihydrate, is within the range of from 0.032±0.030 wt.-%, 0.032±0.026 wt.-%, 0.032±0.024 wt.-%, 0.032±0.020 wt.-%, 0.032±0.016 wt.-%, 0.032±0.012 wt.-%, 0.032±0.008 wt.-%, 0.032±0.004 wt.-%, based on the total weight of the one or more conjugate bases and the one or more conjugate acids and based on the total weight of the composition.

When the buffer is neither sodium citrate nor its dihydrate, but a different buffer, the content of said different buffer preferably amounts to an equivalent content that is necessary to achieve the same buffer capacity at the given pH value as if the buffer would be sodium citrate or its dihydrate in the above content in wt.-%.

In preferred embodiments, the composition according to the invention comprises a buffer comprising one or more conjugate bases and one or more conjugate acids and having a concentration of at least 0.5 mmol/L, more preferably at least 0.6 mmol/L, still more preferably at least 0.7 mmol/L, yet more preferably at least 0.8 mmol/L, and most preferably at least 0.9 mmol/L, based on the total content of the one or more conjugate bases and the one or more conjugate acids and based on the total volume of the composition.

In preferred embodiments, the composition according to the invention comprises a buffer comprising one or more conjugate bases and one or more conjugate acids and having a concentration of not more than 1.5 mmol/L, more preferably not more than 1.4 mmol/L, still more preferably not more than 1.3 mmol/L, and most preferably not more than 1.2 mmol/L, based on the total content of the one or more conjugate bases and the one or more conjugate acids and based on the total volume of the composition.

In preferred embodiments, the composition according to the invention comprises a buffer comprising one or more conjugate bases and one or more conjugate acids and having a concentration within the range of from 0.5 to 1.5 mmol/L, more preferably within the range of from 0.6 to 1.4 mmol/L, still more preferably within the range of from 0.7 to 1.3 mmol/L, and most preferably within the range of from 0.8 to 1.2 mmol/L, based on the total content of the one or more conjugate bases and the one or more conjugate acids and based on the total volume of the composition The buffered pH value of the composition according to the invention is within the range of from 4.0 to 6.0, preferably within the range of from 4.5 to 5.5.

In a preferred embodiment, the composition has a buffered pH value within the range of 4.5±0.5, more preferably 4.5±0.4, still more preferably 4.5±0.3, yet more preferably 4.5±0.2, and in particular 4.5±0.1.

In another preferred embodiment, the composition has a buffered pH value within the range of 5.0±1.0, more preferably 5.0±0.9, still more preferably 5.0±0.8, yet more preferably 5.0±0.7, even more preferably 5.0±0.6 or 5.0±0.5, most preferably 5.0±0.4 or 5.0±0.3, and in particular 5.0±0.2 or 5.0±0.1.

In still another preferred embodiment, the composition has a buffered pH value within the range of 5.5±0.5, more preferably 5.5±0.4, still more preferably 5.5±0.3, yet more preferably 5.5±0.2, and in particular 5.5±0.1.

Preferably, the content of molecular oxygen of the composition, i.e. the content of dissolved molecular oxygen, is not more than 9.0 mg/L, more preferably not more than 7.0 mg/L, still more preferably not more than 5.0 mg/L, yet more preferably not more than 3.0 mg/L, and most preferably not more than 1.0 mg/L, based on the total volume of the composition.

Preferably, the content of molecular oxygen in the composition is not more than 0.2 mg/L, more preferably 0.1 mg/L, still more preferably 0.05 mg/L, based on the total volume of the composition.

In preferred embodiments, the content of molecular oxygen in the composition is not more than 0.20 mg/L, or 0.18 mg/L, or 0.16 mg/L, or 0.14 mg/L, or 0.12 mg/L, or 0.10 mg/L, or 0.09 mg/L, or 0.08 mg/L, or 0.07 mg/L, or 0.006 mg/L, or 0.05 mg/L, or 0.04 mg/L, or 0.03 mg/L, or 0.02 mg/L.

In preferred embodiments, the content of molecular oxygen in the composition is not more than 0.048 mg/L, or 0.046 mg/L, or 0.044 mg/L, or 0.042 mg/L, or 0.040 mg/L, or 0.038 mg/L, or 0.036 mg/L, or 0.034 mg/L, or 0.032 mg/L, or 0.030 mg/L, or 0.028 mg/L, or 0.026 mg/L, or 0.024 mg/L, or 0.022 mg/L, or 0.020 mg/L, or 0.018 mg/L, or 0.016 mg/L, or 0.014 mg/L, or 0.012 mg/L, or 0.010 mg/L.

The composition according to the invention is preferably packaged in containers, e.g. in glass ampoules. The inner space of the container typically comprises at least two phases, namely a liquid phase and a gaseous phase (headspace). As far as the content of molecular oxygen is concerned, the oxygen content in the liquid phase and the oxygen content in the headspace are typically equilibrated. Thus, measuring the content of molecular oxygen in the gaseous phase of the headspace allows drawing conclusions also concerning the content of dissolved molecular oxygen of the liquid phase, i.e. the aqueous composition as such.

In preferred embodiments—when filling 2.0 ml of the composition into a closed glass ampoule having an inner volume of 3.0 ml and containing pure nitrogen gas such that the filled ampoule comprises the composition as a liquid phase and a gaseous phase in a headspace above the liquid phase, and allowing the gas dissolved in the liquid phase and the gas in the gaseous phase to equilibrate—the gaseous phase has a content of molecular oxygen of not more than 2.5% $\nabla$, more preferably not more than 2.4% $\nabla$, still more preferably not more than 2.3% $\nabla$, yet more preferably not more than 2.2% $\nabla$, even more preferably not more than 2.1% $\nabla$, and most preferably not more than 2.0% $\nabla$. In preferred embodiments, under the given conditions, the gaseous phase has preferably a content of molecular oxygen of not more than 1.8% $\nabla$, more preferably not more than 1.6% $\nabla$, still more preferably not more than 1.4% $\nabla$, yet more preferably not more than 1.2% $\nabla$, even more preferably not more than 1.0% $\nabla$, and most preferably not more than 0.8% $\nabla$.

Suitable methods for adjusting and determining the oxygen content of aqueous pharmaceutical compositions are known to the skilled person and suitable measuring devices are commercially available. The oxygen content can be reduced by purging the composition with an inert gas such as nitrogen and/or by subjecting the composition to reduced pressure and/or by purging the headspace of the composition with an inert gas such as nitrogen. Preferably, the oxygen content in the headspace is determined by means of an electrochemical oxygen sensor, e.g. a Head Space Analyzer Orbisphere 510, Hach Lange.

It has been surprisingly found that by reducing the oxygen content of the pharmaceutical composition, the shelf life can be substantially improved, particularly the chemical stability of Tapentadol in the composition at its comparatively low concentrations.

The osmolarity of the composition depends on the content of its constituents and is preferably adjusted during the manufacture of the composition by the addition of an appropriate amount of an isotonizing agent, preferably sodium chloride. Other isotonizing agents such as mannitol or sorbitol can also be added alternatively or additionally. Ionic isotonizing agents are preferred.

Thus, preferably the composition according to the invention comprises an isotonizing agent, more preferably sodium chloride.

Preferably, the content of the sodium chloride is not more than 1.0 wt.-%, more preferably not more than 0.8 wt.-%, still more preferably not more than 0.6 wt.-%, yet more preferably not more than 0.4 wt.-%, most preferably not more than 0.2 wt.-%, and in particular not more than 0.1 wt.-%, based on the total weight of the composition.

In preferred embodiments, the content of the sodium chloride is within the range of from 0.848±0.800 wt.-%, or 0.848±0.700 wt.-%, or 0.848±0.600 wt.-%, or 0.848±0.500 wt.-%, or 0.848±0.400 wt.-%, or 0.848±0.300 wt.-%, or 0.848±0.200 wt.-%, or 0.848±0.100 wt.-%, based on the total weight of the composition.

Preferably, the composition according to the invention does not contain any preservative. For the purpose of the specification, a "preservative" preferably refers to any substance that is usually added to pharmaceutical compositions in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

Preferably, the composition according to the invention does not contain any chelating agents such as EDTA or its sodium or calcium salts. However, the composition according to the invention may contain a citrate buffer and under these circumstances, citric acid and its salts are to be considered as a buffer and not as a chelating agent, though it is known that citric acid and its salt also have a certain degree of chelating capacity.

Preferably, the composition according to the invention does not contain any antioxidants. Examples of antioxidants that are preferably not contained in the composition according to the invention include but are not limited to propyl, octyl and dodecylesters of gallic acid,
butylated hydroxyanisole (BHA), butylated hydroxytoluene (BHT),
ascorbic acid, sodium ascorbate,
monothioglycerol,
potassium or sodium metabisulfite,
propionic acid,
propyl gallate,
sodium bisulfite, sodium sulfite, and
the tocopherols or vitamin E.

Preferably, the composition according to the invention contains neither any preservative nor any antioxidant.

In a preferred embodiment, the composition according to the invention essentially consists of Tapentadol, buffer, isotonizing agent and water.

Particularly preferred embodiments $A^1$ to $A^8$ of the composition according to the invention are summarized in the table here below:

|  | $A^1$ | $A^2$ | $A^3$ | $A^4$ |
|---|---|---|---|---|
| Tapentadol [mg/mL] | 1.0 ± 0.8 | 1.0 ± 0.7 | 1.0 ± 0.6 | 1.0 ± 0.5 |
| buffer [wt.-%] | 0.032 ± 0.030 | 0.032 ± 0.026 | 0.032 ± 0.024 | 0.032 ± 0.020 |
| sodium chloride [wt.-%] | 0.848 ± 0.800 | 0.848 ± 0.700 | 0.848 ± 0.600 | 0.848 ± 0.500 |
| water [wt.-%] | 99.020 ± 0.970 | 99.020 ± 0.900 | 99.020 ± 0.800 | 99.020 ± 0.700 |
| oxygen headspace [% $\nabla$] | ≤2.5% | ≤2.4% | ≤2.3% | ≤2.2% |
| pH value | 5.0 ± 1.0 | 5.0 ± 0.9 | 5.0 ± 0.8 | 5.0 ± 0.7 |

-continued

|  | $A^5$ | $A^6$ | $A^7$ | $A^8$ |
|---|---|---|---|---|
| Tapentadol [mg/mL] | 1.0 ± 0.4 | 1.0 ± 0.3 | 1.0 ± 0.2 | 1.0 ± 0.1 |
| buffer [wt.-%] | 0.032 ± 0.016 | 0.032 ± 0.012 | 0.032 ± 0.008 | 0.032 ± 0.004 |
| sodium chloride [wt.-%] | 0.848 ± 0.400 | 0.848 ± 0.300 | 0.848 ± 0.200 | 0.848 ± 0.100 |
| water [wt.-%] | 99.020 ± 0.600 | 99.020 ± 0.500 | 99.020 ± 0.400 | 99.020 ± 0.300 |
| oxygen headspace [% $\nabla$] | ≤2.1% | ≤2.1% | ≤2.0% | ≤2.0% |
| pH value | 5.0 ± 0.6 | 5.0 ± 0.6 | 5.0 ± 0.5 | 5.0 ± 0.5 |

Preferably, the composition according to the invention has a titration acidity of not more than 1.8 mmol/L, more preferably not more than 1.7 mmol/L, still more preferably not more than 1.6 mmol/L, yet more preferably not more than 1.5 mmol/L, and most preferably not more than 1.4 mmol/L.

Preferably, the composition according to the invention has a titration acidity within the range of from 1.0 to 1.8 mmol/L, more preferably 1.4 to 1.8 mmol/L. Especially in pediatric patients titration acidity is an important parameter in view of the lower blood volume.

Preferably, titration acidity is determined at a CO2 partial pressure of 0 mm Hg under Argon at 37° C. When titrating the composition according to the invention under these conditions with 0.01 M NaOH up to an endpoint of pH 7.4.

In a preferred embodiment, particularly when the composition has a pH value within the range of 5.0±0.5, the titration acidity is preferably within the range of 1.20±0.20 mmol/L, more preferably 1.20±0.10 mmol/L.

In another preferred embodiment, particularly when the composition has a pH value within the range of 4.5±0.5, the titration acidity is preferably within the range of 1.60±0.20 mmol/L, more preferably 1.60±0.10 mmol/L.

In order to satisfy high quality requirements for infusion and injection solutions, respectively, the composition has to exhibit a physiologically acceptable osmolarity and a physiologically acceptable pH.

Isotonic sodium chloride solution (saline), for instance, contains 0.9 wt.-% of sodium chloride and exhibits an osmolarity of 0.308 osmol/L, which is close to the osmolarity of blood.

Preferably, the composition has an osmolarity of at least 0.20 or at least 0.22 osmol/L, more preferably of at least 0.23 osmol/L, still more preferably of at least 0.24 osmol/L, yet more preferably of at least 0.25 osmol/L, most preferably of at least 0.26 osmol/L, and in particular of at least 0.27 osmol/L.

Preferably, the composition has an osmolarity of not more than 0.36 osmol/L, more preferably of not more than 0.34 osmol/L, still more preferably of not more than 0.32 osmol/L, yet more preferably of not more than 0.31 osmol/L, most preferably of not more than 0.30 osmol/L and in particular of not more than 0.29 osmol/L.

In preferred embodiments, the composition has an osmolarity of 0.28±0.08 osmol/L, more preferably of 0.28±0.06 osmol/L, still more preferably of 0.28±0.04 osmol/L, yet more preferably of 0.28±0.03 osmol/L, most preferably of 0.28±0.02 osmol/L, and in particular of 0.28±0.01 osmol/L.

Another aspect of the invention relates to a container comprising the pharmaceutical composition according to the invention, wherein the container is preferably a closed and airtight container. All preferred embodiments that have been defined above in connection with the composition according to the invention analogously also apply to the container according to the invention.

The container according to the invention comprises a distinct volume of the composition according to the invention that is adapted for parenteral administration to the patient. As the aqueous composition according to the invention is typically liquid, it is preferably provided in a container. Prior to parenteral administration, the composition according to the invention is then removed, completely (single dosage) or partially (multiple dosage) from the container.

Preferably, the container is a glass ampoule. Preferably, the container is made from glass of quality type I that satisfies the requirements of Ph. Eur. for parenteral formulations.

Preferably, the container comprises the composition as a liquid phase and a gaseous phase in a headspace above the liquid phase, wherein the gaseous phase has a content of molecular oxygen of not more than 2.5% $\nabla$, more preferably not more than 2.4% $\nabla$, still more preferably not more than 2.3% $\nabla$, yet more preferably not more than 2.2% $\nabla$, even more preferably not more than 2.1% $\nabla$, and most preferably not more than 2.0% $\nabla$. In preferred embodiments, under the given conditions, the gaseous phase has preferably a content of molecular oxygen of not more than 1.8% $\nabla$, more preferably not more than 1.6% $\nabla$, still more preferably not more than 1.4% $\nabla$, yet more preferably not more than 1.2% $\nabla$, even more preferably not more than 1.0% $\nabla$, and most preferably not more than 0.8% $\nabla$.

The container according to the invention may comprise a single dose of Tapentadol or may be multiple dosed. For the purpose of the specification "multiple dosed" preferably means that the container encompasses more than a single dosage unit.

In a preferred embodiment, the container contains the composition according to the invention in a quantity exceeding a single administration dose (dosage unit). Under these circumstances, the container comprises multiple dosage units, i.e. is customized for more than a single administration, preferably by injection.

For example, when the container comprises a multiple dosed injection solution, its overall volume is more than the volume that is to be typically administered at once. Instead, the multiple dosed injection solution is customized for being divided into a multitude of dosage units that are to be administered over a treatment interval typically encompassing several days. The individual dosage units may preferably be separated from the multiple dosage unit by means of a syringe. A typical example for a container according to the invention that comprises multiple dosage units is a preferably sterilized glass container sealed with a septum. Said glass container contains a volume of the pharmaceutical composition well exceeding the individual volume of an individual dosage unit that is intended for at once administration to the patient. For example, when the container has a total volume of 250 mL and the prescribed dosage unit is 25 mL once daily, at day 1 of the treatment interval the patient takes 25 mL so that 225 mL remain in the container;

at day 2 of the treatment interval the patient takes another 25 mL so that 200 mL remain in the container; and so on, until at day 10 the entire amount is taken by the patient.

Preferably, the container contains at least 2, more preferably at least 3, even more preferably at least 5, yet more preferably at least 10, most preferably at least 12, and in particular at least 15 individual dosage units.

In another preferred embodiment, the container comprises a single dosage unit, i.e. only one individual dosage unit. Under these circumstances, the container preferably comprises from 1.0 to 3.0 mL of the composition.

Preferably, the individual dosage units have a volume of 0.25 mL to 3.0 mL, more preferably of 0.5 mL to 2.75 mL, still more preferably of 0.75 mL to 2.5 mL, and most preferably of 1.0 mL to 2.0 mL.

In a preferred embodiment, the individual dosage units have a volume of 1.0±0.9 mL, more preferably of 1.0±0.75 mL, still more preferably 1.0±0.5 mL, yet more preferably of 1.0±0.4 mL, even more preferably of 1.0±0.2 mL, most preferably of 1.0±0.15 mL, and in particular of 1.0±0.1 mL.

In another preferred embodiment, the individual dosage units have a volume of 2.0±0.9 mL, more preferably of 2.0±0.75 mL, still more preferably 2.0±0.5 mL, yet more preferably of 2.0±0.4 mL, even more preferably of 2.0±0.2 mL, most preferably of 2.0±0.15 mL, and in particular of 2.0±0.1 mL.

In still another preferred embodiment, the individual dosage units have a volume of 3.0±0.9 mL, more preferably of 3.0±0.75 mL, still more preferably 3.0±0.5 mL, yet more preferably of 3.0±0.4 mL, even more preferably of 3.0±0.2 mL, most preferably of 3.0±0.15 mL, and in particular of 3.0±0.1 mL.

The one or more individual dosage units that are contained in the container may be customized for administration once, twice, thrice, four times, five times, six times or even more frequently, optionally in regular time intervals.

The composition that is contained in the container may also be customized for a continual administration, preferably by infusion. Preferably, the composition that is contained in the container is adapted for a continual administration for at least 30 minutes or 45 minutes, more preferably for at least 1 h or 2 h, still more preferably for at least 3 h or 4 h, yet more preferably for at least 6 h or 8 h, most preferably for at least 10 h, and in particular for at least 12 h.

Tapentadol is administered in a therapeutically effective amount. The amount that constitutes a therapeutically effective amount varies according to the condition being treated, the severity of said condition and the patient being treated.

Preferably, the amount of Tapentadol that is contained in the individual dosage unit is preferably within the range of from 0.2 to 0.6 mg/kg body weight.

In a preferred embodiment, the amount of Tapentadol that is contained in the individual dosage unit is preferably within the range of from 10 mg to 250 mg, more preferably within the range of from 15 mg to 200 mg, still more preferably within the range of from 20 mg to 150 mg, yet more preferably within the range of from 30 mg to 130 mg, and most preferably within the range of from 40 mg to 115 mg, and in particular within the range of from 50 mg to 100 mg.

In another preferred embodiment, the amount of Tapentadol that is contained in the individual dosage unit is preferably within the range of from 0.1 mg to 60 mg, more preferably within the range of from 0.1 mg to 55 mg, still more preferably within the range of from 0.2 mg to 50 mg.

Preferably, the container according to the invention comprises Tapentadol in an amount within the range of from 1.00 mg to 3.00 mg, based on the weight of Tapentadol free base.

Preferably, the daily dose of Tapentadol is not more than 250 mg, more preferably not more than 225 mg, yet more preferably not more than 200 mg, still more preferably not more than 175 mg, and in particular not more than 150 mg.

Preferably, the daily dose of Tapentadol is at least 15 mg, more preferably at least 20 mg, yet more preferably at least 25 mg, still more preferably at least 30 mg, most preferably at least 35 mg, and in particular at least 40 mg.

The composition according to the invention, particularly when it is contained in the container according to the invention, has an excellent shelf life and storage stability. Thus, preferably, the composition according to the invention is stable upon storage.

Preferably, the composition according to the invention is stable upon storage under accelerated storage conditions at 40° C. and 75% relative humidity for at least 3 months, more preferably at least 6 months. Preferably, stability criteria are in accordance with Ph. Eur. and EMEA guidelines, respectively, preferably according to the edition that is valid in March 2015.

In preferred embodiments, the pH value of the composition after storage under accelerated storage conditions at 40° C. and 75% relative humidity for at least 3 months, more preferably at least 6 months, does not relatively differ by more than ±0.4 pH units, more preferably by not more than ±0.3 pH units, more preferably by not more than ±0.2 pH units, from the initial pH value of the composition prior to storage.

Preferably, the composition is colorless before storage and after storage under accelerated storage conditions at 40° C. and 75% relative humidity for at least 3 months, more preferably at least 6 months. Preferably, the composition is colorless before storage and during/after storage, in particular during/after a storage time of more than three months, preferably of more than 6 months, more preferably of more than 12 months, most preferably of at least for twenty-four months.

In preferred embodiments, the composition has a content of decomposition products of Tapentadol after storage under accelerated storage conditions at 40° C. and 75% relative humidity for at least 3 months, more preferably at least 6 months, of not more than 1.0 wt.-%, more preferably not more than 0.9 wt.-%, still more preferably not more than 0.8 wt.-%, yet more preferably not more than 0.7 wt.-%, even more preferably not more than 0.6 wt.-%, and most preferably not more than 0.5 wt.-%, relative to the total content of Tapentadol that was originally contained in the composition prior to storage and based on the weight of Tapentadol free base. Decomposition products of Tapentadol are preferably analyzed by HPLC.

For the purpose of the specification, it may additionally be distinguished between shelf life and in-use stability. Shelf life preferably refers to the storage stability of a closed container. In-use stability preferably refers to the storage container that contains a multiple dosage unit preparation which has been utilized for the first time. Typically, the shelf life of a multiple dosage unit preparation is much longer than its in-use stability. Preferably, stability criteria are in accordance with Ph. Eur. and EMEA guidelines, respectively, preferably according to the edition that is valid in March 2015.

Preferably, the composition according to the invention, particularly when it is contained in the container according to the invention, exhibits a shelf life under ambient conditions of at least 6 month, more preferably at least 12 months, still more preferably at least 15 months, yet more preferably at least 18 months, most preferably at least 21 months and in particular at least 24 months.

Preferably, the composition according to the invention, particularly when it is contained in the container according to the invention, is provided as a multiple dosage unit preparation that exhibits an in-use stability under ambient conditions of at least 1 week, more preferably at least 2 weeks, still more preferably at least 3 weeks, yet more preferably at least 4 weeks, most preferably at least 5 weeks and in particular at least 6 weeks.

It has been surprisingly found that even at comparatively low concentrations of Tapentadol pH value and content of molecular oxygen can be controlled such that undesired decomposition reactions of Tapentadol can be reduced. No additional excipients are needed for stabilization.

Preferably, the composition according to the invention exhibits an antimicrobial robustness that complies with the requirements of the Ph. Eur., preferably in its version for 2010. Preferably, antimicrobial robustness is achieved against *S. aureus*, Ps. *Aeruginosa*, S. spp., *C. albicans*, and/or *A. niger*, preferably satisfying the requirement of log reduction of 1, preferably 3 after 7 and no increase after 28 days. In a particularly preferred embodiment, antimicrobial robustness is achieved against bacteria satisfying the requirement of log reduction of 3 after 14 days and against molds and yeast of log reduction of 1 after 14 days.

The composition according to the invention, particularly when it is contained in the container according to the invention, exhibits an excellent autoclavability, i.e. it can be subjected to autoclaving under suitable conditions for a suitable period of time without causing significant degradation of Tapentadol under the typically drastic conditions of autoclaving. Preferably, the composition is stable upon autoclaving and preferably exhibits an unaltered pH value upon autoclaving.

Preferably, the composition is stable upon autoclaving for 20 minutes at 121° C. and 2 bar. Preferably, the composition is stable upon autoclaving for 20 minutes at 121° C. and 2 bar and preferably exhibits an unaltered pH value upon autoclaving under these conditions.

Preferably, stability criteria are in accordance with Ph. Eur. and EMEA guidelines, respectively, preferably according to the edition that is valid in March 2015.

In preferred embodiments, the composition according to the invention, particularly when it is contained in the container according to the invention, has a content of decomposition products of Tapentadol after autoclaving of not more than 0.05 wt.-%, more preferably not more than 0.04 wt.-%, and most preferably not more than 0.03 wt.-%, relative to the total content of Tapentadol that was originally contained in the composition prior to autoclaving and based on the weight of Tapentadol free base.

Preferably, the pharmaceutical composition according to the invention is for use in the treatment of pain.

Accordingly, a further aspect of the invention relates to a method for the treatment of pain comprising the parenteral administration of a therapeutically effective amount of the pharmaceutical composition according to the invention as described above, that may be provided in the container according to the invention as described above, to a subject in need thereof.

Furthermore, the invention also relates to the use of Tapentadol or a physiologically acceptable salt thereof for the manufacture of the pharmaceutical composition according to the invention as described above or of the container containing the pharmaceutical composition according to the invention as described above, for the treatment of pain. Preferably, Tapentadol is employed as Tapentadol hydrochloride polymorph form A. Form A of Tapentadol hydrochloride is known from the prior art. In this regard, it can be referred to e.g. US 2007/0213405. Form A is preferably characterized by showing at least one or more X-ray lines (2-theta values) in a powder diffraction pattern when measured using Cu Kα radiation selected from the list comprising 15.1±0.2, 16.0±0.2, 18.9±0.2, 20.4±0.2, 22.5±0.2, 27.3±0.2, 29.3±0.2 and 30.4±0.2

The pain may either be chronic pain or acute pain. Acute pain is preferred.

Preferably, the pain is selected from the group consisting of inflammatory pain, neuropathic pain, visceral pain, labor pain, cancer pain, perioperative and post-operative pain.

In a preferred embodiment, the pain is cancer pain, preferably neuropathic pain being induced by the cancer, including neuropathic pain as a direct result of the cancer on peripheral nerves, or as a side effect of chemotherapy, surgery or radiation injury.

In another preferred embodiment, the pain is perioperative or post-operative (post-surgical) pain.

In still another preferred embodiment, the pharmaceutical composition according to the invention is for use in emergency pain management.

Preferably, the composition according to the invention is for use in the treatment of pain in mammals. Preferably, the mammals are humans. Preferably, the humans are pediatric patients.

For the purpose of the specification, pediatric patients preferably encompass premature infants, newborn infants, infants, children up to the age of 2, children, and adolescents. Preferably, the upper age limit of the pediatric patients is 1, 2, 3, 4, 5, 6, 8, 10, 12, 14, 16 or 17. Preferably, the lower body weight limit of the pediatric patients is 30 kg or 25 kg, more preferably 20 kg or 15 kg, still more preferably 10 kg or 7.5 kg, yet more preferably 5 kg or 3 kg, most preferably 2 kg or 1 kg, and in particular 500 g.

In a preferred embodiment, the composition is adapted for parenteral administration to children having a body weight of 10 to 15 kg, 16 to 20 kg, 21 to 25 kg, 26 to 30 kg, 31 to 35 kg, 36 to 40 kg and/or 41 to 45 kg. In another preferred embodiment, the composition is adapted for parenteral administration to infants or children having a body weight of below 0.5 kg, 0.6 kg to 0.9 kg, 1.0 kg to 1.9 kg, 2.0 kg to 2.9 kg, 3.0 kg to 3.9 kg, 4.0 kg to 4.9 kg, 5.0 kg to 5.9 kg, 6.0 kg to 8.0 kg and/or 8.1 kg to 9.9 kg.

In a preferred embodiment, the pediatric patients are newborn infants. Preferably, the pharmaceutical composition according to the invention is for use in the treatment of acute pain in newborn infants.

In another preferred embodiment, the pediatric patients are premature infants. Preferably, the pharmaceutical composition according to the invention is for use in the treatment of acute pain in premature infants.

Preferably, composition according to the invention, particularly when it is contained in the container according to the invention, is a parenteral formulation selected from the group consisting of injection solutions, injection suspensions, infusion solutions, infusion suspensions, and depot formulations, such as depot injection solutions, depot injection suspensions, implants and infusion pumps.

Compared to oral formulations, parenteral formulations have several advantages, especially when the patient is young or has problems to swallow. They can be exactly dosed, e.g. according to the body weight of the patients, which can be particularly important in pediatric patients. Further, they can be administered by infusion continually over an extended period of time (e. g. 24 h), e. g. by means of an infusion pump.

In a preferred embodiment, the parenteral formulation according to the invention is an infusion solution or infusion suspension.

In another preferred embodiment, the parenteral formulation is an injection solution or injection suspension, which preferably is a single dosage unit form or multiple dosage unit form. Multiple dosage unit injection solutions are preferably contained in an injection vial, whereas single dosage unit forms are preferably contained in a single-use syringe.

In still another preferred embodiment, the parenteral formulation is an implantable device, such as an implantable infusion pump.

In a preferred embodiment, the parenteral formulation according to the invention is a depot formulation (retard formulation).

Preferably, the depot formulation is an infusion solution or infusion suspension, preferably customized for an intramuscular or subcutaneous administration.

Preferably, the depot formulation further contains viscosity-enhancing excipients, such as methylcellulose, gelatine, and polyvidon (polyvinylpyrrolidon) preferably having a molecular weight of not more than 40,000 g/mol. By choosing the appropriate type and the appropriate amount of the viscosity-enhancing excipient, the depot effect of the depot formulation may be influenced.

Preferably, the depot formulation is capable of releasing the drug over time period of at least 12 h or 14 h, more preferably at least 16 h or 18 h, still more preferably at least 20 h, yet more preferably at least 24 h, most preferably at least 36 h, and in particular at least 48 h.

The depot formulation is preferably administered for use in the treatment of acute pain and/or post-surgical pain.

In a preferred embodiment, the composition according to the invention, particularly when it is contained in the container according to the invention, is adapted for local administration. In this regard, local administration includes every administration of the composition to a site which is identical to the site of disorder and/or at least is located nearby. In particular, the local administration has the purpose of delivering Tapentadol directly to the desired site of action, thereby avoiding systemic side-effects. Under these circumstances, the systemic concentration of Tapentadol is preferably kept at a sub-therapeutic concentration; i.e. during the treatment, the systemic concentration of Tapentadol never reaches the level that is required for exhibiting a therapeutic effect when the drug is only administered systemically.

In another preferred embodiment, the composition according to the invention, particularly when it is contained in the container according to the invention, is adapted for systemic administration.

In this embodiment the administration of the composition preferably has the purpose of inducing a systemic action of Tapentadol.

The composition according to the invention is adapted for parenteral administration, preferably by injection or infusion.

The composition according to the invention is adapted for parenteral administration of Tapentadol. The parenteral administration may proceed by infusion or injection.

Infusion solutions or suspensions may be administered continuously, intermittently or patient-controlled. For the administration, infusion devices such as implantable infusion pumps, non-implantable infusion pumps and spinal pumps may be used.

The administration of the composition may proceed intramuscularly, intravenously, subcutaneously, epidurally, intrathecally, intraspinally and/or intracerebroventricularly. Intraveneous administration is particularly preferred.

In a preferred embodiment, the administration proceeds intraspinally, either intrathecally or epidurally, preferably by infusion. The intraspinal administration is especially suitable for treating pain selected from perioperative pain, post-operative pain, labor pain and cancer pain. The dosage of the intraspinal administration may be controlled by means of an infusion pump, either by the patient or by the selection of an appropriate steady or intermittent infusion rate.

In another preferred embodiment, the administration proceeds intramuscularly, intravenously or subcutaneously. This type of administration is especially preferred for the local or regional treatment of pain in distal extremities.

Depot formulations are preferably administered intramuscularly or subcutaneously.

Another aspect of the invention relates to a process for the preparation of the pharmaceutical composition according to the invention or of the container according to the invention, respectively, which process comprises the step of
(a) preparing a mixture comprising Tapentadol or a physiologically acceptable salt thereof, water and a buffer.

In a preferred embodiment, Tapentadol is employed as Tapentadol hydrochloride polymorph form A, which is preferably characterized by showing at least one or more X-ray lines (2-theta values) in a powder diffraction pattern when measured using Cu Kα radiation selected from the list comprising 15.1±0.2, 16.0±0.2, 18.9±0.2, 20.4±0.2, 22.5±0.2, 27.3±0.2, 29.3±0.2 and 30.4±0.2.

Preferably, in the course of manufacturing the composition according to the invention and the container according to the invention, respectively, the intermediate mixtures that are obtained after the process steps are purged with inert gas, preferably nitrogen, in order to discharge dissolved oxygen and to avoid entrainment of oxygen from the gas atmosphere above the composition.

Preferably, step (a) of the process according to the invention comprises a substep relating to the addition of every constituent to the composition, which substep comprises adding, dissolving/mixing and purging with inert gas, preferably nitrogen.

Thus, step (a) of the process according to the invention preferably comprises
- the substep ($a_1$) of providing water for injections and purging with inert gas;
- the substep ($a_2$) of adding buffer, preferably sodium citrate dihydrate, dissolving, and purging with inert gas;
- the substep ($a_3$) of adding Tapentadol, preferably Tapentadol hydrochloride, dissolving, and purging with inert gas;
- the substep ($a_4$) of adding isotonizing agent, preferably sodium chloride, dissolving, and purging with inert gas;
- the substep ($a_5$) of adding acid, preferably hydrochloric acid, mixing, and purging with inert gas; and
- the substep ($a_6$) of adding further water for injections, mixing, and purging with inert gas.

Substeps ($a_1$) to ($a_6$) may be performed in numerical order or in any other order.

Preferably, the process according to the invention comprises one or more additional steps selected from the group consisting of (b) purging the mixture with an inert gas; and/or
(c) filtering the mixture through a filter, preferably of an average pore size of not more than 1.0 µm, more preferably not more than 0.5 µm, still more preferably not more than 0.2 µm; and/or
(d) filling the mixture into a suitable container, preferably a glass ampoule; and/or
(e) autoclaving the mixture at elevated temperature and elevated pressure, preferably at 121° C. and 2 bar for at least 20 minutes.

Preferably, steps (b), (c), (d) and/or (e) are performed in alphabetical order.

The invention also relates to a composition or a container that is obtainable by the process according to the invention as described above.

Another aspect of the invention relates to a kit comprising the container according to the invention as described above and a packaging, wherein the container is packaged by the packaging. The container may be regarded as a primary packaging of the composition, whereas the packaging may be regarded as a secondary packaging of said primary packaging.

Thus, when the composition according to the invention is contained in a container such as a glass ampoule, said container is preferably further packaged by a packaging. Preferably, the packaging contains printed information and/or provides a barrier to light.

Preferably, the packaging is made of a material that is intransparent to visual light.

Preferably, the packaging is disposable. Suitable packaging materials are known to the skilled person and include but are not limited to paper, cardboard, plastics, and metal foil. Preferably, the packaging comprises or essentially consists of cardboard.

Preferably, the composition which is contained in the container and packaged by the packaging is photostable.

In preferred embodiments, the content of decomposition products of Tapentadol in the composition after subjecting the kit for 24 hours to UV radiation at 540 Wh/m$^2$ and an illumination of 1320 kL×h is not more than 0.05 wt.-%, more preferably not more than 0.04 wt.-%, and most preferably not more than 0.03 wt.-%, relative to the total content of Tapentadol that was originally contained in the composition prior to subjecting the composition to UV radiation and based on the weight of Tapentadol free base.

Another aspect of the invention relates to the use of Tapentadol or a physiologically acceptable salt thereof for the preparation of a pharmaceutical composition according to the invention as described above or of a container according to the invention as described above. Preferably, Tapentadol is employed as Tapentadol hydrochloride polymorph form A, which is preferably characterized by showing at least one or more X-ray lines (2-theta values) in a powder diffraction pattern when measured using Cu Kα radiation selected from the list comprising 15.1±0.2, 16.0±0.2, 18.9±0.2, 20.4±0.2, 22.5±0.2, 27.3±0.2, 29.3±0.2 and 30.4±0.2.

The following examples further illustrate the invention but are not to be construed as limiting its scope.

Example 1—Preparation of Composition and Container

The following pharmaceutical composition (50 L) was prepared and subsequently filled into glass ampoules (2.00 mL):

| amount | per ampoule | wt.-% |
| --- | --- | --- |
| Tapentadol HCl | 2.33 mg | |
| equivalent weight relative to Tapentadol free base | 2.00 mg | 0.0997 |
| sodium citrate dihydrate | 0.64 mg | 0.0319 |
| sodium chloride | 17.00 mg | 0.8475 |
| hydrochloric acid solution 1N | ~2.18 mg | q.s. |
| sodium hydroxide solution 1N | q.s. | q.s. |
| water | ad 2.00 mL | |
| pH value | 5.0 ± 0.5 | |
| total volume | 2.00 mL | |
| total weight | 2006 mg | |

Water for injection was weighed in a stainless steel container and purged with nitrogen. Sodium citrate dihydrate was weighed in a suitable container and subsequently added to the water for injection while purging. Tapentadol hydrochloride for parenteral use was weighed in a suitable container and subsequently added to the sodium citrate solution while purging with nitrogen. Sodium chloride was weighed in a suitable container and subsequently added to the solution while purging with nitrogen.

The pH value was measured and adjusted to 5.0 by using 1N hydrochloric acid. If necessary, 1N sodium hydroxide solution was added to readjust the pH to the target value. The remaining water was added to the solution while purging with nitrogen. The pH value was measured again.

The solution was filtered using a filter with 0.2 µm pores (Fluorodyne® KA3DFLP1, polyvinylidene fluoride, Pall). The filtered solution was filled (Fill and seal-machine AFV 6015, Bausch & Strobel) into cleaned (Washing machine AWU 8000, Bausch & Strobel) and sterilized (Sterilization tunnel DST 8000, Bausch & Strobel) type I clear glass ampoules while gassing with nitrogen. The ampoules were closed by a welding and cutting process (Fill and seal-machine AFV 6015, Bausch & Strobel).

The fill weight of the ampoules was measured and the ampoules were autoclaved at 121° C., 2 bar for 20 minutes (Belimed autoclave IV, Belimed). The ampoules were cleaned from the outside (Washing machine DAR150, Seidenader), visually controlled (EISAI AIM 287, Eisai) and subjected to a leak test at high voltage (Densok HDB II, Nikka-Densok).

The thus obtained compositions in the containers were stable upon autoclaving and had an excellent shelf life.

Example 2—Storage Stability (pH, Color, Decomposition of Tapentadol)

A pharmaceutical composition according to the invention and a comparative composition were prepared in accordance with Example 1. The relevant information concerning the two compositions are summarized here below:

| | comparative | inventive |
| --- | --- | --- |
| sodium citrate dihydrate | 0.015 wt.-% (2.76 g in 18.46 kg) | 0.03 wt.-% (7.36 g in 23.07 kg) |
| pH range according to specification | 6.0 to 7.5 | 4.5 to 5.5 |
| content of molecular oxygen in headspace according to specification | 5% ∇ | 2% ∇ |
| measured | | 0.7% ∇ |

The storage stability was investigated. The results are summarized in the table here below:

Comparative Composition 1:

|   |   | color of solution | pH value | purity, Σ decomposition products |
|---|---|---|---|---|
| start |   | colorless | 7.2 | 0.06% |
| 1 | 25° C./60% r.h. | colorless | 7.1 | 0.20% |
|   | 40° C./75% r.h. | colorless | 7.1 | 0.58% |
| 3 | 25° C./60% r.h. | colorless | 7.5 | 0.38% |
|   | 30° C./75% r.h. | colorless | 7.5 | 0.62% |
|   | 40° C./75% r.h. | Sample 1: BG7 Sample 2: <GG6, >GG7 | 7.7 | 1.51% |
| 6 | 25° C./60% r.h. | colorless | 7.5 | 0.51% |
|   | 30° C./75% r.h. | colorless | 7.6 | 0.93% |
|   | 40° C./75% r.h. | GG4 | 7.6 | 2.88% |

Inventive Composition 1:

|   |   | color of solution | pH value | purity, Σ decomposition products |
|---|---|---|---|---|
| start |   | colorless | 5.2 | n.d. |
| 1 | 25° C./60% r.h. | colorless | 5.2 | n.d. |
|   | 40° C./75% r.h. | colorless | 5.2 | n.d. |
| 3 | 25° C./60% r.h. | colorless | 5.1 | <0.05% |
|   | 40° C./75% r.h. | colorless | 5.2 | <0.05% |
| 6 | 25° C./60% r.h. | colorless | 5.0 |   |
|   | 40° C./75% r.h. | colorless | 5.1 |   |
| 9 | 25° C./60% r.h. | colorless | 4.9 |   |
| 12 | 25° C./60% r.h. | colorless | 5.0 |   |
| 18 | 25° C./60% r.h. | colorless | 5.1 |   |

Regarding the color of the solution, the codes BG7, GG4, GG6 and GG7 refer to The Munsell Book of Color (Munsell Color Macbeth Division of Kollmorgan Instruments Corporation).

Example 3—Storage Stability (Photostability)

The inventive composition according to Example 1 in 2 ml clear glass ampoules (glass type I) (primary packaging) was subjected to a photostability test according to ICH Q1B investigating color, clarity and degradation (Illumination at 250 W/m$^2$). Irradiation was performed up to 24 h corresponding to 540 Wh/m2 and 1320 kL×h (ICH Q1B requirement: not less than 200 Wh/m2 and not less than 1200 kL×h). In parallel, the primary packaging was placed into a carboard box as secondary packaging.

The experimental results are summarized in the table here below:

As demonstrated by the above data, color did not change over 24 hours. The degradation products increased. After 8 h irradiation the degradation products were still within specification but failed the limits after 24 hours. 24 h irradiation in the secondary packaging cardboard box, however, did not result in any changes compared to the initial testing.

In addition, Tapentadol 1 mg/mL solution for injection packaged in ampules was submitted over 4 days to a total of 24 h day light irradiation on a window sill in order to evaluate the comparability between artificial irradiation and normal daylight. The extent of degradation is similar to 6 h artificial irradiation (UV: 135 Wh/m$^2$, Illumination: 330 kL×h). The secondary packaging, however, provided sufficient light protection.

The invention claimed is:

1. An aqueous pharmaceutical composition for parenteral administration comprising Tapentadol or a physiologically acceptable salt thereof and a buffer, wherein:
    the concentration of the Tapentadol or a physiologically acceptable salt thereof is within the range of from 0.10 to 8.00 mg/m L, based on the weight of Tapentadol free base and based on the total volume of the aqueous pharmaceutical composition;
    the pH value of the aqueous pharmaceutical composition is within the range of from 4.0 to 6.0;
    the Tapentadol or a physiologically acceptable salt thereof is the only antimicrobial preservative;
    the buffer comprises at least one conjugate base and at least one conjugate acid;
    and the at least one conjugate base comprises a conjugate base selected from the group consisting of citrate, hydrogencitrate, and dihydrogencitrate; and the at least one conjugate acid comprises citric acid; and
    the aqueous pharmaceutical composition is an injection solution, an injection suspension, an infusion solution, an infusion suspension, or a depot formulation.

2. The aqueous pharmaceutical composition according to claim 1, wherein:
    the aqueous pharmaceutical composition is stable upon autoclaving; and
    the aqueous pharmaceutical composition optionally exhibits an unaltered pH value upon autoclaving.

3. The aqueous pharmaceutical composition according to claim 2, wherein:
    the aqueous pharmaceutical composition is stable upon autoclaving for 20 minutes at 121° C. and 2 bar; and
    the aqueous pharmaceutical composition optionally exhibits an unaltered pH value upon autoclaving for 20 minutes at 121° C. and 2 bar.

|   | 0 hours | 2 hours UV: 45 Wh/m$^2$, Illum: 110 kL × h | 4 hours UV: 90 Wh/m$^2$, Illum: 220 kL × h | 6 hours UV: 135 Wh/m$^2$, Illum: 330 kL × h | 8 hours UV: 180 Wh/m$^2$, Illum: 440 kL × h | 24 hours UV: 540 Wh/m$^2$, Illum: 1320 kL × h | | 24 hours irradiation on window sill |
|---|---|---|---|---|---|---|---|---|
| packaging | primary | primary | primary | primary | primary | primary | secondary | primary |
| color and clarity | clear colorless solution | — | — | — | — | clear colorless solution | — | — |
| sum of degradation products | n.d. | n.d. | 0.12 | 0.23 | 0.31 | 1.00 | n.d. | 0.25 | n.d. = not detectable or below reporting threshold
— = test not performed

4. The aqueous pharmaceutical composition according to claim 1, wherein any molecular oxygen present in the aqueous pharmaceutical composition is present at not more than 9.0 mg/L based on the total volume of the aqueous pharmaceutical composition.

5. The aqueous pharmaceutical composition according to claim 1, wherein any molecular oxygen present in the aqueous pharmaceutical composition is present at not more than 0.2 mg/L based on the total volume of the aqueous pharmaceutical composition.

6. The aqueous pharmaceutical composition according to claim 1, wherein the pH value is within the range of from 4.5 to 5.5, optionally before autoclaving for 20 minutes at 121° C. and 2 bar and after autoclaving for 20 minutes at 121° C. and 2 bar.

7. The aqueous pharmaceutical composition according to claim 1, wherein:
the buffer has a concentration of at least 0.5 mmol/L, based on the total content of the at least one conjugate base and the at least one conjugate acid and based on the total volume of the aqueous pharmaceutical composition.

8. The aqueous pharmaceutical composition according to claim 1, wherein:
the buffer has a concentration of not more than 1.5 mmol/L, based on the total content of the at least one conjugate base and the at least one conjugate acid and based on the total volume of the aqueous pharmaceutical composition.

9. The aqueous pharmaceutical composition according to claim 1, wherein:
the buffer has a concentration of not more than 1.5 mmol/L, based on the total content of the at least one conjugate base and the at least one conjugate acid and based on the total volume of the aqueous pharmaceutical composition.

10. The aqueous pharmaceutical composition according to claim 1, wherein the Tapentadol or a physiologically acceptable salt thereof is Tapentadol hydrochloride.

11. The aqueous pharmaceutical composition according to claim 1, wherein the concentration of the Tapentadol or a physiologically acceptable salt thereof is within the range of 1.0±0.5 mg/mL based on the weight of Tapentadol free base and based on the total volume of the aqueous pharmaceutical composition.

12. The aqueous pharmaceutical composition according to claim 1, wherein the aqueous pharmaceutical composition further comprises an isotonizing agent.

13. The aqueous pharmaceutical composition according to claim 12, wherein the isotonizing agent is sodium chloride.

14. The aqueous pharmaceutical composition according to claim 1, wherein the aqueous pharmaceutical composition has a titration acidity of not more than 1.8 mmol/L.

15. The aqueous pharmaceutical composition according to claim 1, wherein:
the aqueous pharmaceutical composition does not comprise an antioxidant;
the aqueous pharmaceutical composition does not comprise a chelating agent; or
the aqueous pharmaceutical composition comprises neither an antioxidant nor a chelating agent.

16. A container comprising the aqueous pharmaceutical composition according to claim 1.

17. The container according to claim 16, wherein the container is a glass ampoule.

18. The container according to claim 16, wherein the volume of the aqueous pharmaceutical composition from 1.0 to 3.0 mL.

19. The container according to claim 16, wherein:
the aqueous pharmaceutical composition comprises a liquid phase and a gaseous phase;
the gaseous phase is disposed in a headspace above the liquid phase;
any molecular oxygen present in the liquid phase is present at not more than 2.5% $\nabla$.

20. The aqueous pharmaceutical composition according to claim 1, wherein the pH value is within the range of 5.0±0.5.

21. The aqueous pharmaceutical composition according to claim 20, wherein the pH value is within the range of from 4.9 to 5.2.

22. The aqueous pharmaceutical composition according to claim 1, wherein the aqueous pharmaceutical composition is colorless and remains colorless on storage at 40° C. and 75% relative humidity for at least 3 months.

* * * * *